United States Patent [19]

Duncan

[11] Patent Number: 4,481,942
[45] Date of Patent: Nov. 13, 1984

[54] INFANT ARM RESTRAINT

[76] Inventor: Thomas A. Duncan, 155 Enwood Dr., Charlotte, N.C. 28214

[21] Appl. No.: 72,157

[22] Filed: Sep. 4, 1979

[51] Int. Cl.³ ............................................ A61F 13/00
[52] U.S. Cl. ................................................... 128/133
[58] Field of Search ................ 128/DIG. 15, 133–135

[56] References Cited

U.S. PATENT DOCUMENTS

| 2,606,554 | 8/1952 | Simon | 128/133 |
| 3,695,258 | 10/1972 | Castle | 128/87 R |
| 3,696,810 | 10/1972 | Gaylord, Jr. | 128/DIG. 23 |
| 4,078,560 | 3/1978 | Hill | 128/133 |

OTHER PUBLICATIONS

Attorney Dictionary of Medicine and Word Finder, Schmidt, M.D., Matthew Bender and Co., New York, N.Y. 10017, "Allergen–Allergy", pp. 126–128, 1980, originally published in 1962.

Primary Examiner—C. Fred Rosenbaum
Assistant Examiner—J. L. Kruter
Attorney, Agent, or Firm—Bell, Seltzer, Park & Gibson

[57] ABSTRACT

This invention relates to an arm restraint for application around the elbow of an infant to restrict movement of the infant's hands from certain areas. The arm restraint comprises a stiffening member formed of flexible plastic sheet material of predetermined dimensions suitable for being formed into a generally cylindrical configuration about the arm of the infant. A washable fabric covering extends over opposite surfaces of the stiffening member and encloses the stiffening member therein to present a soft, clean, washable, nonallergenic surface for contacting the arm of the infant, and is preferably permanently secured to the underlying stiffening member by means of stitching. Securement means is provided on the arm restraint to permit readily fastening the arm restraint in place in a generally cylindrical configuration about the arm of the infant.

2 Claims, 4 Drawing Figures

U.S. Patent  Nov. 13, 1984  4,481,942
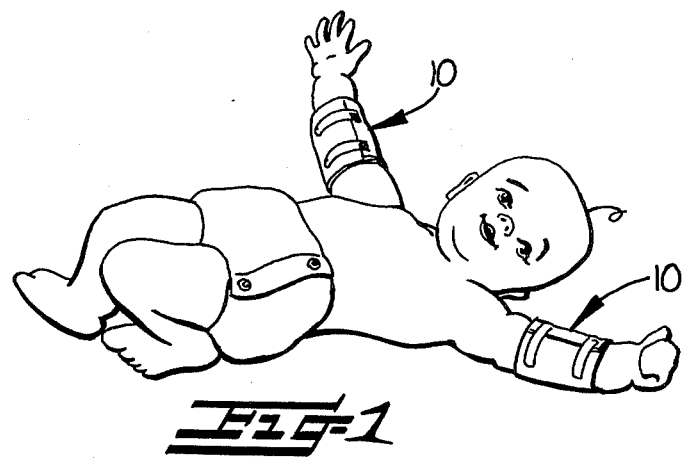
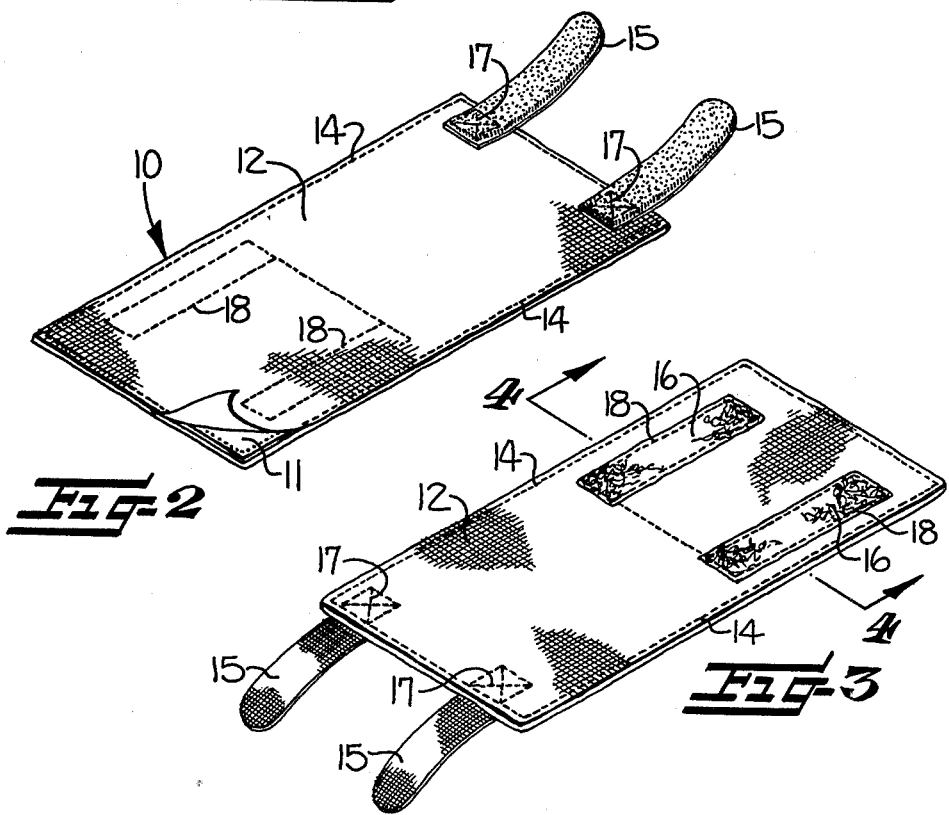

INFANT ARM RESTRAINT

FIELD OF THE INVENTION

This invention relates to a restraint device for application to the arm of an infant.

BACKGROUND OF THE INVENTION

After surgery is performed on an infant, such as facial surgery for example, there is usually a need to restrain the infant's hands from reaching his face where he could pull at bandages or stitches and possibly injure himself. Similarly, when an infant is being fed intravenously, it is necessary to restrict movement of the infant's arms to prevent him from pulling at the I.V. tubes. To those ends, arm restraints have been developed which can be applied around the arm of the infant to prevent the arm from bending at the elbow.

For example, one known type of arm restraint includes a fabric cover having pockets therein for receiving stiffening members, such as wooden tongue depressors. The arm restraint is wrapped about the elbow of the infant and secured in place by straps or ties extending from the arm restraint. A somewhat similar device is shown in Simon U.S. Pat. No. 2,606,554. One of the problems and disadvantages of this known type of arm restraint is that it is difficult to apply to the infant's arm, and usually requires two persons, one to hold the arm restraint in place and hold the infant, the other to fasten the ties. When the arm restraint becomes soiled, it is necessary to remove the stiffening members to permit laundering or sterilizing the cover and to replace the same after laundering. When the stiffening members inadvertently are left in the cover during laundering, they may become broken or damaged. However, when they are removed for laundering, they often become lost.

In U.S. Pat. Nos. 3,010,452; 3,115,132; 4,070,027; 4,078,560; and 4,142,522 there are disclosed a number of other types of arm restraints which have been proposed. However, none of these arm restraints are apparently intended to be laundered or sterilized. Further, these devices allow the infant's skin to come into direct contact with foam or other plastic material, which is not only uncomfortable but may cause an irritation or rash on the sensitive skin of an infant.

SUMMARY OF THE INVENTION

The present invention overcomes the problems of the aforementioned prior arm restraints and provides an arm restraint which may be readily subjected to laundering or sterilizing and which presents a soft, clean, washable, nonallergenic surface for contacting the arm of the infant.

The arm restraint of the present invention comprises a stiffening member formed of a flexible plastic sheet material of predetermined dimensions suitable for being formed into a generally cylindrical configuration about the arm of the infant with opposite ends of the stiffening member overlapping. A washable fabric covering extends over opposite surfaces of the stiffening member and encloses the stiffening member therein to present a soft, clean, washable, nonallergenic surface for contacting the arm of the infant, and securement means is provided on the arm restraint to permit easily securing the arm restraint in a generally cylindrical configuration about the arm of the infant. Preferably, the arm restraint has stitching which extends through the fabric covering and the stiffening member for permanently securing the fabric cover to the stiffening member. The thus constructed arm restraint is capable of withstanding repeated laundering or sterilizing operations without the necessity of removing the interior stiffening member as has heretofore been necessary.

Preferably, the stiffening member is secured in place with the use of strips of hook and loop (Velcro-type) fastening material. One strip of the hook and loop fastener material is carried by the arm restraint and extends longitudinally beyond the end of the arm restraint, and an area of complementary fastening material is provided on the outer surface of the arm restraint and positioned for cooperating with the other strip of fastening material for securing the arm restraint in a generally cylindrical configuration about the arm of the infant.

BRIEF DESCRIPTION OF THE DRAWINGS

Some of the features and advantages of the invention having been described, others will become apparent as the description proceeds, when taken in connection with the accompanying drawings, in which:

FIG. 1 is a perspective view showing an infant wearing the arm restraint device of the present invention;

FIG. 2 is a perspective view showing the one side of the arm restraint, with one corner thereof peeled open for purposes of illustration to reveal the interior construction thereof;

FIG. 3 is a perspective view showing the opposite side of the arm restraint; and FIG. 4 is a cross-sectional view taken substantially along the line 4—4 of FIG. 3.

DESCRIPTION OF THE ILLUSTRATED EMBODIMENT

Referring now more particularly to the drawings, the arm restraint of the present invention is indicated generally by the reference character 10, and is shown in FIG. 1 as it is typically applied to the infant's arm. As illustrated, the arm restraint 10 is of a generally rectangular configuration having a length greater than its width and is of predetermined dimensions suitable for being rolled into a generally cylindrical configuration about an axis extending parallel to the width dimension of the arm restraint so as to thus surround the arm of an infant at the elbow and thereby restrain the arm from bending at the elbow. The precise dimensions may vary depending on the size of the infant for whom it is intended, but generally the length dimension ranges from above seven to eleven inches and the width dimension from about three to about seven inches. Preferably, the arm restraint does not cover the entire arm from armpit to wrist, as in some of the prior arm restraint constructions, since this is uncomfortable and can cause irritation. Preferably, and as illustrated, the width dimension is such as to extend only about one to two inches on each side of the elbow. It is important that the arm restraint be of sufficient length so as to completely surround the arm of the infant with opposite ends of the arm restraint overlapping one another to thereby provide sufficient stiffness and to restrain the arm from bending at the elbow.

The arm restraint includes an interior stiffening member 11 formed of flexible plastic sheet material of a rectangular configuration corresponding substantially to the overall dimensions of the arm restraint and having rounded corners. The stiffening member 11 should be relatively stiff, yet deformable so as to be capable of being rolled or formed into a curved or cylindrical configuration. When so formed, the inherent stiffness of the material resists bending in a direction perpendicular to the axis about which the stiffening member is formed. A preferred material for forming the stiffening member is a flexible vinyl plastic sheet material having a thickness on the order of about 0.035 inches. This material provides the requisite stiffness for serving as a stiffening member and is capable of withstanding the temperatures of washing, drying, or sterilizing without degradation or damage to the plastic and without taking a permanent set.

The stiffening member is covered on all sides with a washable fabric covering 12, which may be of woven or knitted construction. The fabric covering 12 serves for presenting a soft, clean, washable, nonallergenic surface for contacting the arm of the infant and to prevent the infant's arm from coming into direct contact with the plastic stiffening member 11, since such contact may cause irritation or a rash on the sensitive skin of an infant. The fabric is preferably formed of yarns containing hygroscopic fibers, such as cotton, so as to be readily absorbent and to assist in wicking any moisture away from the skin of the infant to prevent irritation.

Preferably, the fabric covering 12 comprises a single piece of fabric which is folded over one of the edges of the stiffening member 11, and with the raw edges of the fabric being folded inside along the remaining three sides of the stiffening member to present a neat, finished appearance to the arm restraint. The thus assembled fabric covering is permanently attached to the underlying stiffening member by one or more rows of stitching extending through the fabric covering and the underlying stiffening member. As illustrated, a row of stitching 14 extends adjacent all four edges of the arm restraint so as to provide a secure and permanent attachment of the fabric covering material 12 to the stiffening member 11, while securing the raw edges of the fabric in place folded inside the arm restraint.

The arm restraint is held in place around the infant's arm by means of elongate self-fastening strips 15, 16 of hook and loop or similar fastener material. Hook and loop or similar type fasteners sold under the trademark Velcro are representative of the fasteners which may be used. As illustrated, one or more strips 15 of Velcro-type material is secured to one end of the arm restraint and extends longitudinally therebeyond. Preferably, the strips are secured by stitching 17 extending through the fabric and the underlying stiffening member. Complementary strips 16 of fastener material are secured to the outer surface of the arm restraint and are positioned for cooperating with the strips 15 when the arm restraint is rolled into a cylindrical configuration with opposite ends thereof overlapping. The strips 16 are secured to the arm restraint by stitching 18 extending through the fabric covering 12 and the underlying stiffening member 11. As illustrated, the stitching 18 also extends transversely of the arm restraint and intermediate the two strips 16, and serves to additionally secure the fabric covering 12 to the stiffening member and to prevent shifting or bunching relative to the stiffening member. As illustrated, the Velcro strips 16 provided on the exterior surface of the arm restraint are of the fibrous type and the complementary strips 15 extending from the end of the arm restraint are of the hook type. While two cooperating pairs of strips 15, 16 are shown in the illustrated embodiment, it will be understood that a single cooperating pair of strips may suffice for a narrower arm restraint while three or more cooperating pairs of strips may be desirable for use on wider arm restraints.

From the foregoing it will be readily seen that an arm restraint constructed in accordance with the present invention has numerous advantages over the arm restraint devices which are presently known. Among these advantages, it is significant to note that the arm restraint of the present invention provides a clean, absorbent, soft, nonirritating fabric surface for contacting the sensitive and tender skin of the infant, and that the arm restraint is capable of withstanding repeated machine washing, drying, or even sterilizing operations without requiring disassembly and without damage to the stiffening member component thereof. The arm restraint is further characterized by being of simple and relatively inexpensive construction and by being quite easy to apply to or remove from the arm of the infant.

In the drawings and specification there has been set forth a preferred embodiment of the invention, and although specific terms are employed, they are used in a generic and descriptive sense only and not for purposes of limitation.

What is claimed is:

1. An arm restraint for application around the elbow of an infant and constructed so as to completely surround the arm of the infant at the elbow and to prevent the arm from bending at the elbow so as to thereby keep the infant's hands away from certain areas, as for example his face, following facial surgery, said arm restraint being characterized by ease of application to the infant's arm, by being comfortable and nonirritating to the tender skin of the infant, and by being capable of withstanding repeated laundering or sterilizing operations, said arm restraint comprising a stiffening member formed of a thin sheet material having sufficient flexibility to permit being formed into a cylindrical configuration but having sufficient stiffness so as to resist bending in a direction perpendicular to the axis of the cylindrical configuration, said sheet material comprising a nonporous plastic material capable of withstanding the temperature of washing, drying or sterilizing without degradation or without damage to the plastic material and without taking a permanent set, and said stiffening member being of a generally rectangular configuration having a length dimension greater than its width dimension, the width dimension being less than the distance between the wrist and the armpit of an infant, and the length dimension being greater than the circumference of the arm of an infant, the width and length dimensions of the stiffening member thus enabling the stiffening member to be formed into a generally cylindrical configuration about an axis parallel to the width dimension to encircle and completely surround the arm of the infant at the elbow and with opposite ends of the stiffening member overlapping to thereby prevent bending of the arm at the elbow, and with the stiffening member extending a short distance on opposite sides of the elbow but not so far as the wrist or armpit to thus avoid discomfort and irritation of the infant, a washable fabric covering extending over opposite surfaces of said stiffening member and enclosing the stiffening member therein and presenting a soft, clean, washable surface for contacting the arm of the infant, said fabric covering being formed of hygroscopic fibers so as to be readily absorbent and to assist in wicking any moisture away from the skin of the infant to prevent irritation, at least one row of stitching extending through the fabric covering and the underlying stiffening member adjacent the periphery of the arm restraint for permanently securing the fabric covering to the underlying stiffening member, at least one elongate strip of hook and loop fastener material positioned adjacent one longitudinal end of the arm restraint and extending longitudinally therebeyond, and including stitching extending through said strip and through the underlying fabric covering and stiffening member for securing said strip to the arm restraint, and at least one strip of complementary hook and loop fastener material positioned on the outer surface of the arm restraint medially of opposite ends thereof and extending in a longitudinal direction and positioned for cooperating with said other strip of fastening material for securing the arm restraint in a generally cylindrical configuration about the arm of an infant with opposite ends of the arm restraint overlapping one another.

2. An arm restraint for application around the elbow of an infant and constructed so as to completely surround the arm of the infant at the elbow and to prevent the arm from bending at the elbow so as to thereby keep the infant's hands away from certain areas, as for example his face, following facial surgery, said arm restraint being characterized by ease of application to the infant's arm, by being comfortable and nonirritating to the tender skin of the infant, and by being capable of withstanding repeated laundering or sterilizing operations, said arm restraint comprising a stiffening member formed of a nonporous vinyl plastic sheet material having a thickness on the order of about 0.035 inches and having sufficient flexibility to permit being formed into a cylindrical configuration but having sufficient stiffness so as to resist bending in a direction perpendicular to the axis of the cylindrical configuration, said vinyl sheet material being capable of withstanding the temperature of washing, drying or sterilizing without degradation or without damage to the plastic material and without taking a permanent set, and said stiffening member being of a generally rectangular configuration having a length dimension greater than its width dimension, and width dimension being from about three to about seven inches and less than the distance between the wrist and the armpit of an infant, and the length dimension being from about seven to about eleven inches and greater than the circumference of the arm of an infant, the length and width dimensions of the stiffening member thus enabling the stiffening member to be formed into a generally cylindrical configuration about an axis parallel to the width dimension to encircle and completely surround the arm of the infant at the elbow and with opposite ends of the stiffening member overlapping to thereby prevent bending of the arm at the elbow, and with the stiffening member extending a short distance on opposite sides of the elbow but not so far as the wrist or armpit to thus avoid discomfort and irritation to the infant, a washable fabric covering extending over opposite surfaces of said stiffening member and enclosing the stiffening member therein and presenting a soft, clean, washable surface for contacting the arm of the infant, said fabric covering being formed of hygroscopic fibers so as to be readily absorbent and to assist in wicking any moisture away from the skin of the infant to prevent irritation, at least one row of stitching extending through the fabric covering and the underlying stiffening member adjacent the periphery of the arm restraint for permanently securing the fabric covering to the underlying stiffening member, at least one elongate strip of hoop and loop fastener material positioned adjacent one longitudinal end of the arm restraint and extending longitudinally therebeyond, and including stitching extending through said strip and through the underlying fabric covering and stiffening member for securing said strip to the arm restraint, and at least one strip of complementary hook and loop fastener material positioned on the outer surface of the arm restraint medially of opposite ends thereof and extending in a longitudinal direction and positioned for cooperating with said other strip of fastening material for securing the arm restraint in a generally cylindrical configuration about the arm of an infant with opposite ends of the arm restraint overlapping one another.

* * * * *